United States Patent [19]

Leckie

[11] Patent Number: 4,926,928

[45] Date of Patent: May 22, 1990

[54] PROTECTIVE DEVICE OF RESTRAINING ROD PRODUCED IN CONTINUOUS CASTING AND ROLLING PROCESS

[75] Inventor: James H. Leckie, Huntington, Ind.

[73] Assignee: Essex Group, Inc., Fort Wayne, Ind.

[21] Appl. No.: 760,202

[22] Filed: Jul. 29, 1985

[51] Int. Cl.⁵ .............................................. B22D 11/12
[52] U.S. Cl. .................................... 164/452; 164/150; 164/154; 164/417; 164/476
[58] Field of Search ............... 164/452, 150, 154, 263, 164/417, 476

[56] References Cited

U.S. PATENT DOCUMENTS

| | | |
|---|---|---|
| 3,279,000 | 10/1966 | Cofer et al. . |
| 3,552,161 | 1/1971 | Garbe et al. . |
| 3,682,234 | 8/1972 | Vogel . |
| 3,731,512 | 5/1973 | Vogel et al. . |
| 3,752,220 | 8/1973 | Hofmann et al. ............... 164/263 X |
| 3,881,151 | 4/1975 | Bigelow, Jr. . |
| 3,944,911 | 3/1976 | Tornblom . |
| 4,146,837 | 3/1979 | Bashkirov . |
| 4,324,515 | 4/1982 | Ehling . |

Primary Examiner—Kuang Y. Lin

[57] ABSTRACT

A protective device for use in a continuous casting and rolling process for protecting an eddy current detectoor. A rod arresting means is actuated when a break in the continuous rod or bar is detected. This prevents rod having fins or projections from passing into and damaging an eddy current detector.

5 Claims, 3 Drawing Sheets

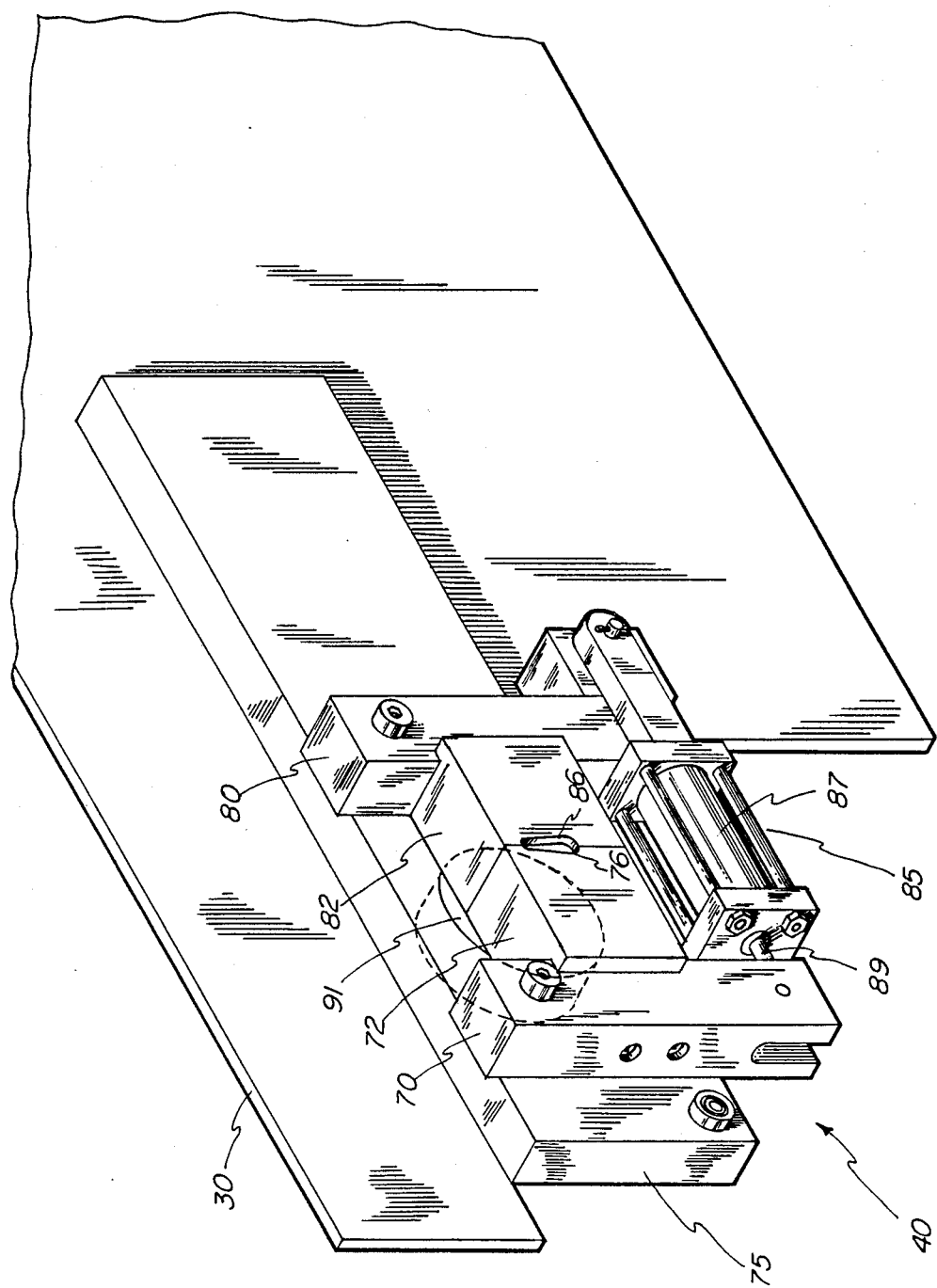

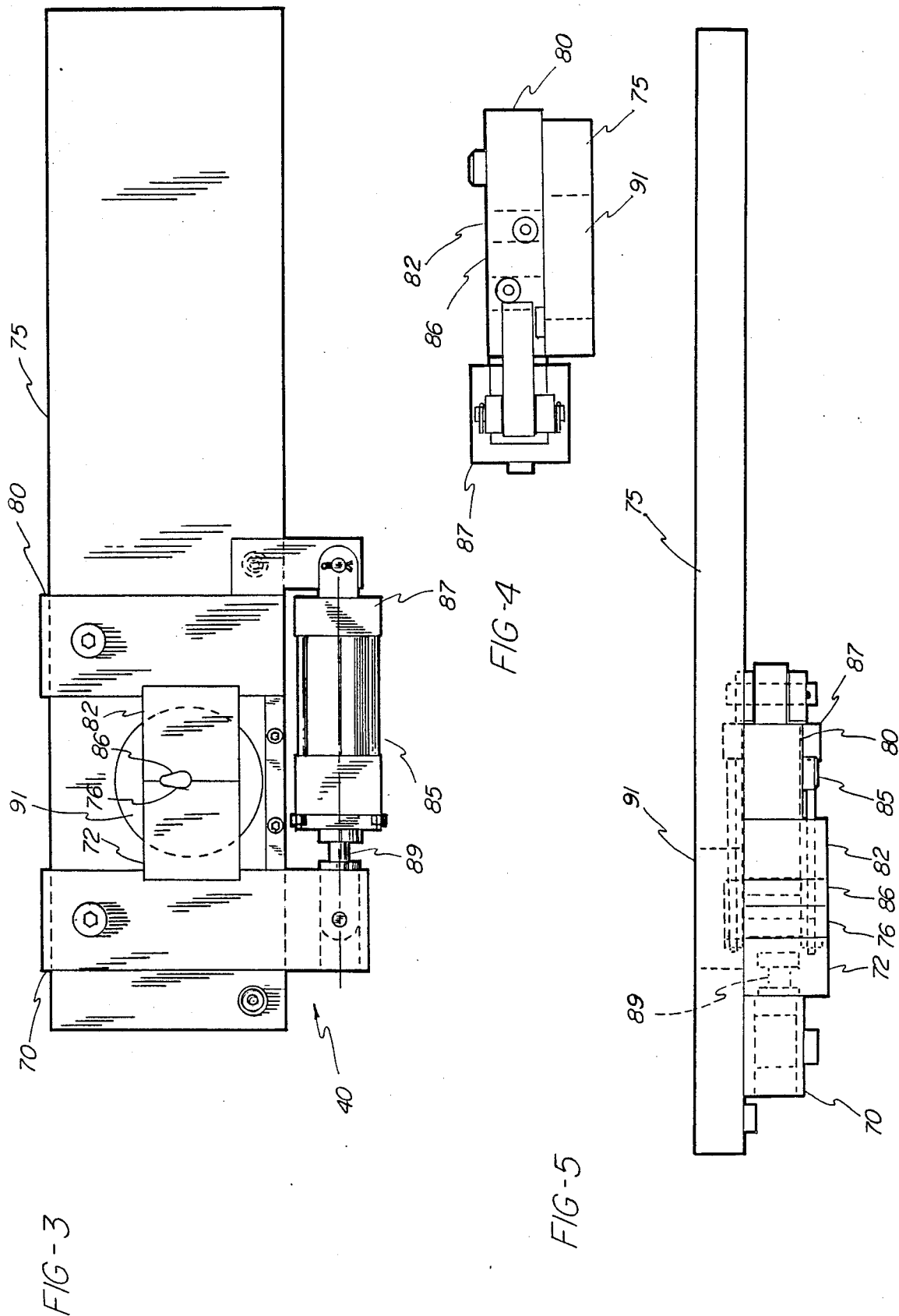

PROTECTIVE DEVICE OF RESTRAINING ROD PRODUCED IN CONTINUOUS CASTING AND ROLLING PROCESS

TECHNICAL FIELD

The field of art to which this invention pertains is the continuous casting and rolling of metal bar, in particular, a protective device for restraining rod produced in a continuous casting and rolling operation.

BACKGROUND ART

Processes and apparatuses for the continuous casting of metal bar are well known in the art. A continuous casting apparatus typically comprises an internally and externally cooled casting wheel having a center about which it rotates. The wheel has a continuous groove about its periphery which serves as one part of a molding cavity. The apparatus additionally comprises an endless belt which is positioned to be in close contact with the periphery of the wheel during a segment of its rotation, thereby forming a molding cavity. Molten metal is continuously cast into the cavity formed between the rotating wheel and the moving belt. As the metal contained in the cavity formed between the wheel and the belt rotates with the wheel angularly about its center, heat is removed from the metal and a solidified bar is formed. The bar is removed from the rotating wheel and directed to mills for further processing.

The metals which are typically cast in a continuous casting system are metals which are malleable ductile and easily formable by rolling into rod such as aluminum and copper.

As the cast bar is discharged from the wheel, it is typically rolled while still at a temperature within a conventional hot-working temperature range. In the rolling process, the overall longitudinal and transverse dimensions (cross-sectional area) of the bar are reduced in stages by passing through successive conventional rolling mill stands, until a round rod having the desired diameter is produced. The bar length increases accordingly as the cross-sectional area is reduced. Rolling mill stands conventionally comprise machines having grooved rolls which are mechanically loaded. The grooved rollers size the bar and pull it through the rolling mill.

Since the bar comes off of the casting wheel at a relatively slow translational speed, and since the translational speed of the bar increases with each successive size reduction, the bar is preferably under a tensile load during the rolling process. If there is a break in the bar after it comes off the wheel, the bar on the distal side of the break will continue to move through the rolling mill stands due to the action of the mill rolls. It is known, however, that the corresponding loss of tension caused by the bar break results in excess metal being pushed to the outside of the bar or rod. This metal takes the form of protuberances or fins on the side of the rod as it exits from the last mill stand.

When circular rod is produced by a continuous casting and rolling system, it is desirable to test the rod for surface defects prior to coiling. The rod produced by continuous casting and rolling processes is typically used in high speed wire drawing manufacturing processes where it is drawn at high speed through dies to produce fine diameter wires such as magnet wire. It is known that surface defects in the rod will produce defective or inferior wire.

It is known in the art that defects in rod can be detected by an eddy current detector. An eddy current detector is an electrical device producing a magnetic field thereby inducing currents in metal rod passing therethrough. The detector typically has a hollow cylindrical frame through which the rod passes. Irregularities in the rod produce abnormal eddy currents which are detected and correlated to defects. The clearance between the sidewalls of the detector and the rod is mechanically close so that extreme projections or deformities of the rod will damage the detector. This situation occurs when a continuous rod breaks thereby resulting in fins on the rod.

Continuous casting apparatuses are disclosed in U.S. Pat. Nos. 3,279,000 and 3,682,234, the disclosures of which are incorporated by reference.

A method and apparatus for the detection of eddy current impeding flaws in moving electrically conductive objects such as rod is disclosed in U.S. Pat. No. 3,881,151. Sensing coils in the apparatus measure changes in eddy currents induced by magnetic fields signifying flaws in rod passing through the detector. The flaws can comprise voids, ferrous inclusions, breaks, cracks, etc.

U.S. Pat. No. 3,552,161 discloses a method of protecting a mill from rod irregularities in a continuous casting process. A sensing means energizes a cutting device which severs the rod and diverts it before it can enter and possibly damage a mill.

U.S. Pat. No. 3,731,512 discloses a means for severing a defective rod or bar in a rolling mill to prevent the bar from being further processed.

Eddy current detectors are expensive and it is not practical to have numerous spares. When spares are not available, the process must be run without eddy current detectors. The rod produced is then of unknown surface quality and may not be suitable for use in certain high speed wire drawing applications.

Accordingly, what is needed in this art is a method of manufacturing rod in a continuous casting and rolling process so that an eddy current detector used in the process will be protected against damage when there is a rod break in the continuous rod or bar during the processing.

DISCLOSURE OF INVENTION

An improved method of manufacturing rod in a continuous casting and rolling process is disclosed. Molten copper is cast into bar on a continuous casting apparatus. The cast bar is rolled to form rod through a series of rolling mill stands. The rod is tested for surface defects by moving it through an eddy current detector and is then coiled.

The improvement comprises using a protective means between the last rolling mill stand and the eddy current detector to arrest the movement of the rod through the detector upon the occurrence of a break in the continuously cast bar, thereby protecting the detector from damage.

Yet another aspect of this invention is an apparatus for arresting the translational motion of rod through an eddy current detector in a continuous casting and hot rolling process. The apparatus comprises a means for arresting the rod, a means for actuating the rod arresting means, a means for activating the actuating means, and a mounting means.

The foregoing and other descriptions and advantages of the present invention will become more apparent from the following description and accompanying drawings.

BRIEF DESCRIPTION OF THE DRAWINGS

FIG. 2 is a perspective view illustrating the apparatus of the present invention.

FIG. 3 is a front view of the apparatus of the present invention.

FIG. 4 is a side view of the apparatus of the present invention.

FIG. 5 is a plan view illustrating the apparatus of the present invention.

BEST MODE FOR CARRYING OUT THE INVENTION

Figure 1:
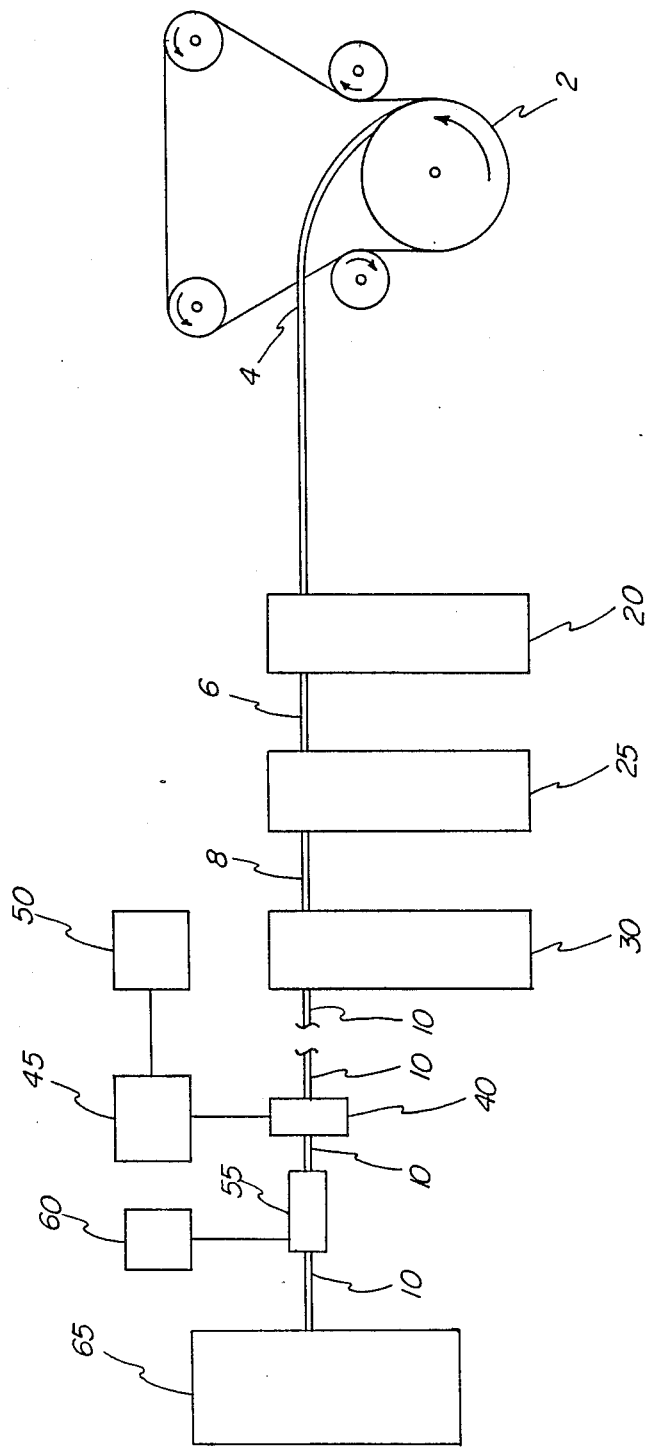
FIG. 1 shows a schematic of a typical continuous casting and hot rolling process utilizing the eddy current detector protective apparatus of the present invention.

As best illustrated in the process diagram of FIG. 1, a continuously cast bar 4 is produced on a continuous casting apparatus 2. The bar moves through a first rolling stand 20 which reduces the cross sectional area of the bar 4 to a bar 6. The bar 6 moves through a rolling mill stand 25 wherein it is reduced in size (cross-sectional area) to a rod 8. The rod 8 moves through a rolling mill stand 30 where it is further reduced in cross sectional area to a rod 10 which then moves through an eddy current detector 55. The rolling mill stands 20, 25 and 30 are conventional mills known in the art containing grooved rolls for shaping and reducing the cross sectional of bar and rod passing therethrough. Although only three roller mill stands are shown in FIG. 1, it will be understood that a greater number may be used if desired and that stand 30 will be the final stand. The preferred shape is circular. The eddy current detector 55 is a conventional, annular type eddy current detector device similar to that disclosed in U.S. Pat. No. 3,881,151 through which the rod 10 passes. A conventional control means 60 interprets changes in eddy currents in the rod and displays the number of surface defects monitored by the eddy current detector 55. The rod 10 passes through the eddy current detector 55 to coiling means 65. The rod 10 prior to passing through the eddy current detector 55 passes through a protective apparatus 40. A conventional activator means 45 activates protective apparatus 40 if there is a break in the bar 4, the bar 6, the rod 8 or the rod 10 anytime during the processing. Typically, in the operation of a continuous casting and rolling process rod or bar may break or the rod or bar may be cut if defective rod or bar is being produced to prevent further processing of the defective rod or bar and to segregate the defective rod or bar. The actuator means 45 is in turn activated by an activator means 50. The activator means 50 may be responsive to the operation of cutting means such as are disclosed in U.S. Pat. No. 3,731,512.

The process may be employed whenever a break anywhere in the continuous bar or rod occurs. The consequent loss in tension caused by a break will cause the rod 10 to have fins, projections or protuberances (collectively referred to hereinafter as projections) which could potentially damage the eddy current detector 55. The tolerances between the rod and the inner surface of the eddy current detector are typically about 0.070". The actuator means 50 signals the actuator means 45 to activate the apparatus 40 wherein the apparatus 40 arrests the translational movement of the rod 10 preventing the rod 10 from moving through the eddy current detector 55 causing the rod 10 to stop within the rolling mill stands. The waste rod 10 is discarded or recycled.

The process is started again by threading the bar and rod through the mills 20, 25 and 30 and through the deactivated apparatus 40, the eddy current detector 55 and the coiling means 65.

The protective apparatus 40 is illustrated in perspective view in FIG. 2 and is preferably mounted to the mill stand 30. The apparatus as illustrated in FIG. 3 comprises a first vertical member 70 which is pivotally attached at its top end to a support frame 75. A second vertical member 80 is displaced horizontally therefrom and is similarly pivotally attached at its top end to the frame 75. A jaw 72 is firmly attached on one side to the side of the member 70. The jaw 72 has a groove 76 on its other side. A jaw 82 is similarly attached to the side of member 80. The jaw 82 has a similar groove 86 on its other side, so that the jaw 72 and the groove 76 are aligned with the jaw 82 and the groove 86. The air cylinder assembly 85 comprises a cylinder 87 and an extendable piston rod 89 operable by a piston (not shown). The rod 89 is pinned at its end to the bottom of the member 70. The cylinder 87 of the cylinder assembly 85 is attached by suitable pivotable means to the bottom of the member 80. The frame 75 contains an opening 91 therethrough for receiving and passing through rod on a continuous basis. The apparatus 40 is shown in a closed position wherein the movement of a rod 10 would be arrested in the grooves 76 and 86 of the jaws 72 and 82, forceably preventing the rod from moving by mechanically interfering with the movement of the rod 10 through the grooves 76 and 86. Cylinder assembly 85 is normally in an extended position causing members 70 and 80 to rotate clockwise and counter clockwise respectively thereby separating jaw 72 from jaw 82 and permitting rod to travel through frame 75 unrestrained. When an activator means 50 signals an actuator means 45 to stop the forward motion of rod, the actuator means activates cylinder assembly 85 to a retracted position, causing jaws 72 and 82 to come together around the rod contained in the cavity formed by the grooves 76 and 86 thereby preventing the rod from moving through frame 75 and and through the eddy current device 55, thus protecting the eddy current device 55 from any potential damage. It will be appreciated that the grooves 76 and 86 can be properly sized so that when the jaws 72 and 82 are in a retracted position, properly sized rod will pass through the cavity formed by the grooves 76 and 86, while oversized rod will be arrested.

The actuator means 45 can be any number of conventional, known actuator means such as solenoid valves, relays, etc. (preferably, a solenoid valve). Cylinder assembly 85 is preferably an air cylinder, however, it will be similarly appreciated by one skilled in the art that this device can be replaced with an electrical-mechanical system, or a hydraulic system, etc. The activator means 50 could comprise any conventional detector means such as an optical detector, an eddy current detector, etc. It will be appreciated that the actuator means 45 can be manually activated by conventional manual means such as switches, etc., upon the visual observance by an operator of a break in the rod or bar. The apparatus 40 may be constructed of any material known in the art capable of withstanding the forces and temperatures present in a conventional rolling mill operation in which hot bar is connected to rod.

Although this invention has been shown and described with respect to detailed embodiments thereof it will be understood by those skilled in the art that various changes in form and detail thereof may be made without departing from the spirit and scope of the claimed invention.

I claim:

1. A method of manufacturing rod by continuously casting a molten metal on a continuous casting apparatus to form a continuous bar, the bar is rolled through a series of rolling mill stands to form rod, the rod is passed through an eddy current detector to detect flaws, and then coiled, characterized by:

sensing a break in said bar or rod, and activating a protective device between said mill stands and said eddy current detector to prevent any projections formed on the rod by the break in said bar or rod from damaging said eddy current detector.

2. The method of claim 1 further characterized by:

arresting said rod when a first projection contacts said protective device.

3. A continuous casting apparatus for producing a continuous rod having a plurality of mill stands for forming said continuous rod and an eddy current detector disposed downstream of said mill stands to detect surface flaws in said continuous rod characterized by:

means for detecting a break in said continuous rod, and means for protecting said eddy current detector disposed between said mill stands and said eddy current detector and activated by said detecting means upon a break in said rod to prevent any projections formed on the rod due to said break from damaging said eddy current detector.

4. The casting apparatus of claim 3 wherein said protecting means is further characterized by a means for clamping said rod.

5. The casting apparatus of claim 4 wherein said clamping means is further characterized by having a dimension wherein a rod may pass through said clamping means until a projection on said rod reaches said clamping means.

* * * * *